United States Patent
Ozawa et al.

(10) Patent No.: US 8,454,812 B2
(45) Date of Patent: Jun. 4, 2013

(54) CAPILLARY ELECTROPHORESIS APPARATUS

(75) Inventors: Miho Ozawa, Abiko (JP); Ryoji Inaba, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 864 days.

(21) Appl. No.: 11/819,191

(22) Filed: Jun. 26, 2007

(65) Prior Publication Data

US 2008/0041724 A1    Feb. 21, 2008

(30) Foreign Application Priority Data

Jun. 27, 2006    (JP) .................................. 2006-175993

(51) Int. Cl.
   *G01N 27/447*    (2006.01)
(52) U.S. Cl.
   CPC .................... *G01N 27/447* (2013.01)
   USPC ........................................ 204/601; 204/600
(58) Field of Classification Search
   CPC ........ G01N 27/44704; G01N 27/44721; G01N 27/4473
   USPC ................ 204/450, 451, 453, 455, 470, 600, 204/601, 603, 604, 605, 615; 215/235, 379, 215/248; 222/249; 137/247; 422/102
   See application file for complete search history.

(56) References Cited

U.S. PATENT DOCUMENTS

| 2,913,138 | A | * | 11/1959 | Swick ............................ 220/219 |
| 3,657,541 | A | * | 4/1972 | Deutsch et al. ............. 250/252.1 |
| 5,552,087 | A | * | 9/1996 | Zeheb et al. ............... 252/408.1 |
| 6,016,683 | A | * | 1/2000 | Betts et al. ...................... 73/1.03 |
| 6,027,627 | A | * | 2/2000 | Li et al. .......................... 204/603 |
| 6,854,888 | B1 | * | 2/2005 | Brown et al. .................... 383/80 |
| 2004/0003994 | A1 | * | 1/2004 | Shoji et al. ..................... 204/451 |
| 2005/0191211 | A1 | * | 9/2005 | Bindrim ........................ 422/68.1 |
| 2006/0070880 | A1 | * | 4/2006 | Goudberg et al. ............ 204/450 |
| 2007/0086923 | A1 | * | 4/2007 | Li et al. ......................... 422/100 |

FOREIGN PATENT DOCUMENTS

| JP | 8-226921 | 9/1996 |
| JP | 2001-242140 | 9/2001 |
| JP | 2001-281221 | 10/2001 |
| JP | 2006-119158 | 5/2006 |

OTHER PUBLICATIONS

Nakayama et al "Bio Experiment Illustrated" Viewed-buy-eye Experiment Note Series pp. 13-16 kabushiki-kaisha Syujyunsha, Japan Feb. 20, 2001.
Japanese Office Action, issued in Japanese Patent Application No. JP 2006-175993 dated on Sep. 9, 2008.

* cited by examiner

*Primary Examiner* — J. Christopher Ball
(74) *Attorney, Agent, or Firm* — McDermott Will & Emery LLP

(57) ABSTRACT

A capillary electrophoresis apparatus capable of efficiently using a polymer in a polymer container is provided. The present invention relates to a mechanism for efficiently using the polymer in the polymer container in a capillary electrophoresis apparatus for the electrophoresis with a separation medium filled in a capillary. According to the present invention, since the polymer in the polymer container is not contacted with the air, deterioration of the polymer by oxidation can be prevented.

3 Claims, 8 Drawing Sheets

CAPILLARY ELECTROPHORESIS APPARATUS

BACKGROUND OF THE INVENTION

1. Field of the Invention

The present invention relates to the technique for storing an electrophoresis medium in a capillary electrophoresis apparatus.

2. Description of the Related Art

Since the capillary electrophoresis apparatus have a high heat dissipation capacity so as to apply a high voltage compared with the slab gel electrophoresis apparatus conventionally used, they have the advantage of a high speed electrophoresis. Therefore, the capillary electrophoresis apparatus have been utilized for various separation analysis measurement such as the analysis of DNA and proteins.

Many of the capillary electrophoresis apparatus recently used have a mechanism for automatically replacing the polymers as the separation media. The DNA sequencers commercially available as Prism 310, 3100, 3730 (product name) from Applied Biosystems, U. S. A. automatically fill the capillary with the polymer using a syringe and a pump.

Japanese Patent Application Laid-Open No. 2001-242140
Japanese Patent Application Laid-Open No. 2001-281221

In the capillary electrophoresis apparatus, an extremely expensive polymer is used as the separation medium. The polymer is stored in general in a polymer bottle. A tube for pumping up the polymer into a pump extends up to the bottom of the polymer bottle so that the polymer at the bottom in the polymer bottle is used first and the polymer in the vicinity of the surface remains until the end. However, since the surface of the polymer is exposed to the air, the polymer in the vicinity of the surface is denatured or deteriorated.

The present inventor has found out that the polymer remaining until the end in the polymer bottle is denatured or deteriorated so that the efficient use of the polymer is prevented.

SUMMARY OF THE INVENTION

An object of the present invention is to provide a capillary electrophoresis apparatus capable of efficiently using the polymer in the polymer container.

The present invention relates to a mechanism for efficiently using the polymer in the polymer container in a capillary electrophoresis apparatus for the electrophoresis with a separation medium filled in a capillary. According to the present invention, since the polymer in the polymer container is not contacted with the air, deterioration of the polymer by oxidation can be prevented.

According to the present invention, the polymer in the polymer container can be used efficiently.

DESCRIPTION OF THE PREFERRED EMBODIMENTS

Figure 1:
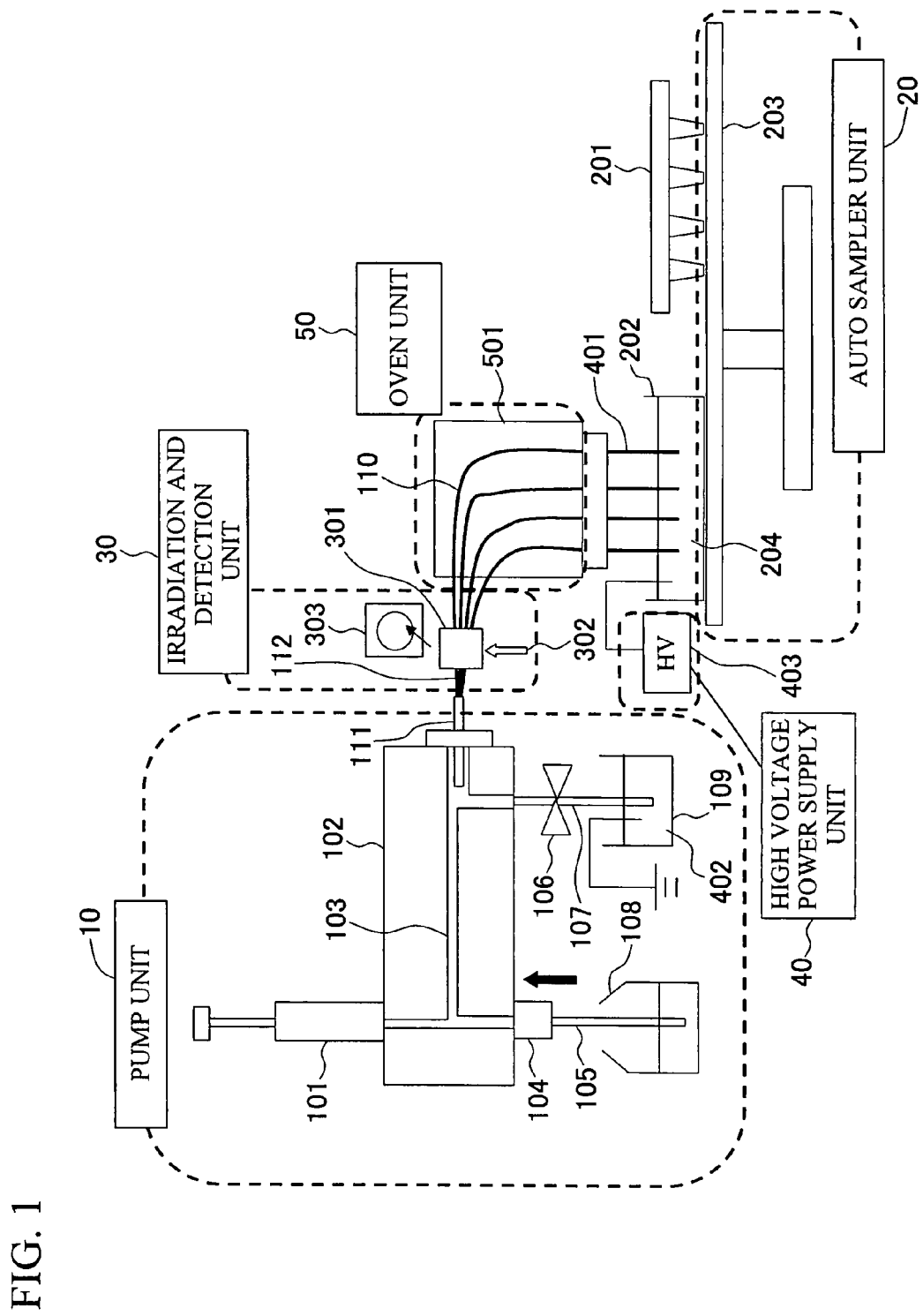
FIG. 1 is a chart showing an example of a capillary electrophoresis apparatus according to the present invention.

FIG. 1 shows an example of the configuration of a capillary electrophoresis apparatus according to the present invention. The capillary electrophoresis apparatus of this example includes a pump unit 10, an auto sampler unit 20, an irradiation and detection unit 30, a high voltage power supply unit 40, and an oven unit 50.

The pump unit 10 comprises a syringe 101, a polymer block 102, a check valve 104, a channel switching valve 106, a polymer bottle 108 and a buffer container 109 and fills the capillary with a separation medium such as a polymer. The buffer container 109 is provided with an anode 402. The operation of the pump unit will be explained later in detail.

A tube 111 mounted on a capillary head 112 at the top end of a capillary array 110 is connected with the polymer block 102, and the lower end of the capillary array 110 is provided with a capillary end of sample injection side electrode 401.

The auto sampler unit 20 includes an auto sampler 203 for conveying to or from a capillary end of sample injection 204, a sample container 201 with the sample dispensed, a buffer reservoir 202 for storing a buffer solution containing a dissolved electrolyte, a container containing washing water for washing the capillary top end or a container containing a waste liquid.

The irradiation and detection unit 30 includes a light source of a laser, a LED, or the like for irradiating an exciting light 302 to a capillary detection area 301, and a signal detecting mechanism 303 for detecting a fluorescence from the capillary detection area 301. The high voltage power supply unit 40 includes a high voltage power supply 403 for applying a high voltage between the capillary end of sample injection side electrode 401 and the anode 402. The oven unit 50 includes an oven 501 for storing the capillary array 110.

Figure 2:
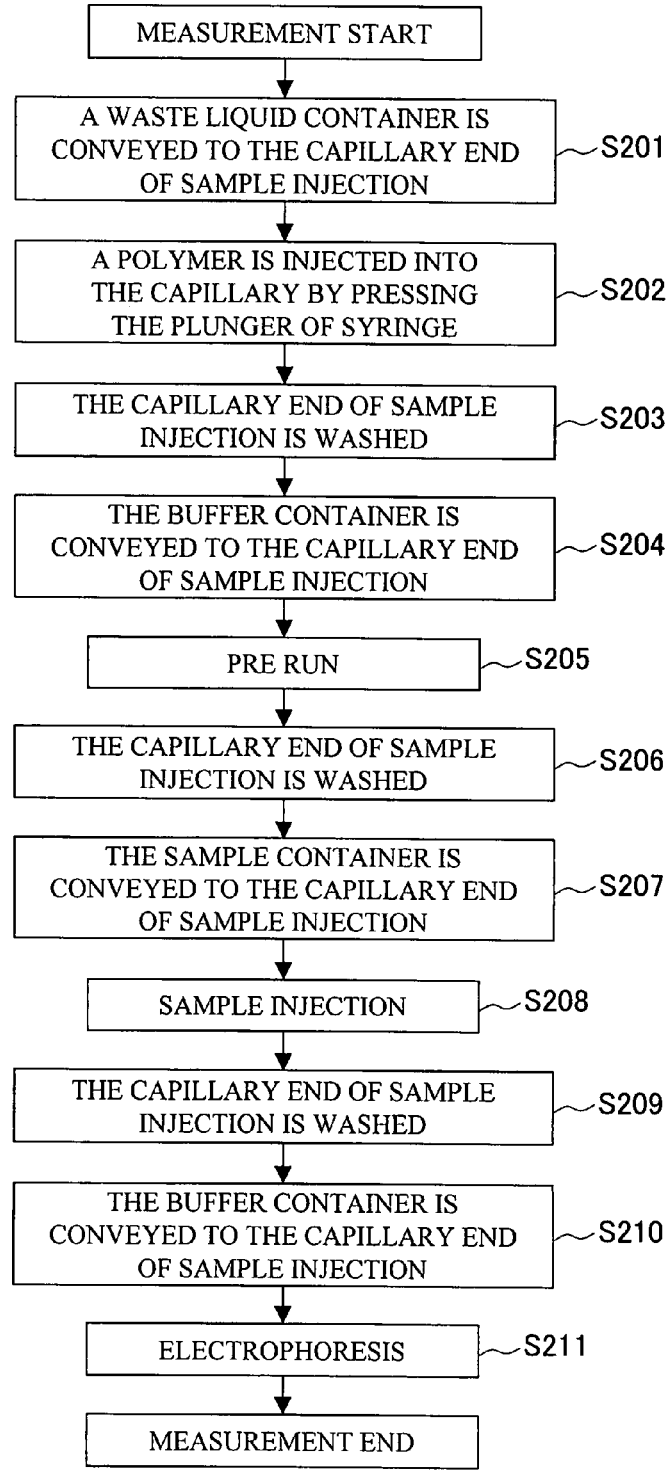
FIG. 2 is a chart showing the flow of measurement of the capillary electrophoresis by a capillary electrophoresis apparatus according to the present invention.

With reference to FIG. 2, operation of the capillary electrophoresis apparatus according to the present invention will be explained. In the step S201, the waste liquid container is conveyed by the auto sampler 203 to the capillary end of sample injection 204. The waste liquid container stores water for dissolving the waste separated medium pushed out from the capillary. In the step S202, the syringe 101 is operated for pushing out the used separation medium into the waste liquid container and injecting a new separation medium into the capillary.

In the step S203, the washing water container is conveyed to the capillary end of sample injection 204 by the auto sampler 203 for washing the capillary end of sample injection 204. In the step S204, the buffer container is conveyed to the capillary end of sample injection 204. In the step S205, a voltage is applied to the capillary without sample injection for carrying out the pre run.

In the step S206, the washing water container is conveyed to the capillary end of sample injection 204 by the auto sampler 203 for washing the capillary end of sample injection 204. In the step S207, the sample container is conveyed to the capillary end of sample injection 204 by the auto sampler 203 for soaking the capillary end of sample injection 204 in the sample solution in the sample container.

In the step 208, a voltage is applied to the capillary for injecting the sample into the capillary electrokinetically. In the step S209, the washing water container is conveyed to the capillary end of sample injection 204 by the auto sampler 203 for washing the capillary end of sample injection 204. In the step S210, the buffer container is conveyed to the capillary end of sample injection 204 by the auto sampler 203. In the step S211, electrophoresis is carried out by applying an electrophoresis voltage to the capillary.

Figure 3:
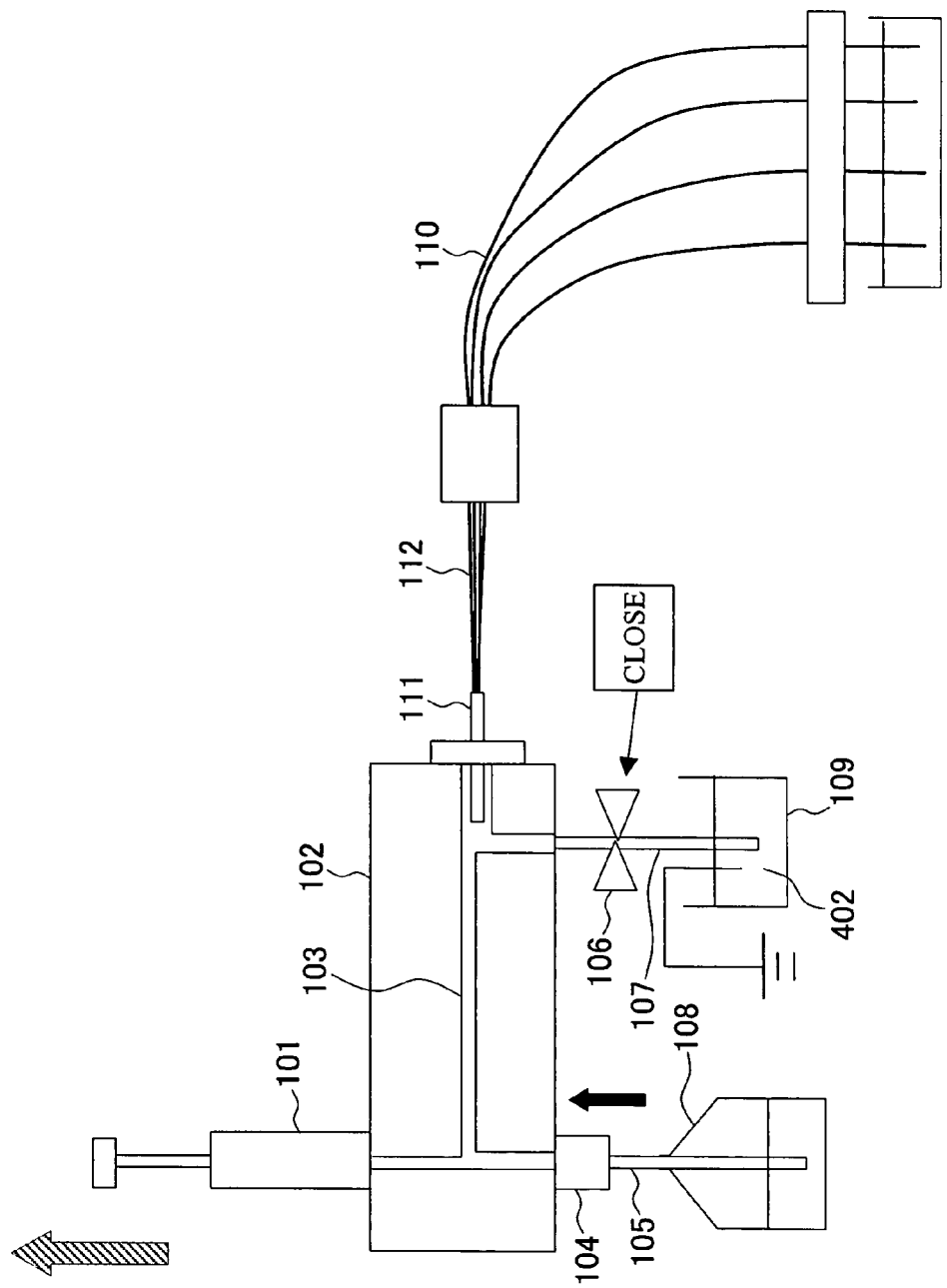
FIG. 3 is a diagram for explaining the method for filling the capillary with the polymer in the capillary electrophoresis apparatus according to the present invention.
Figure 4:
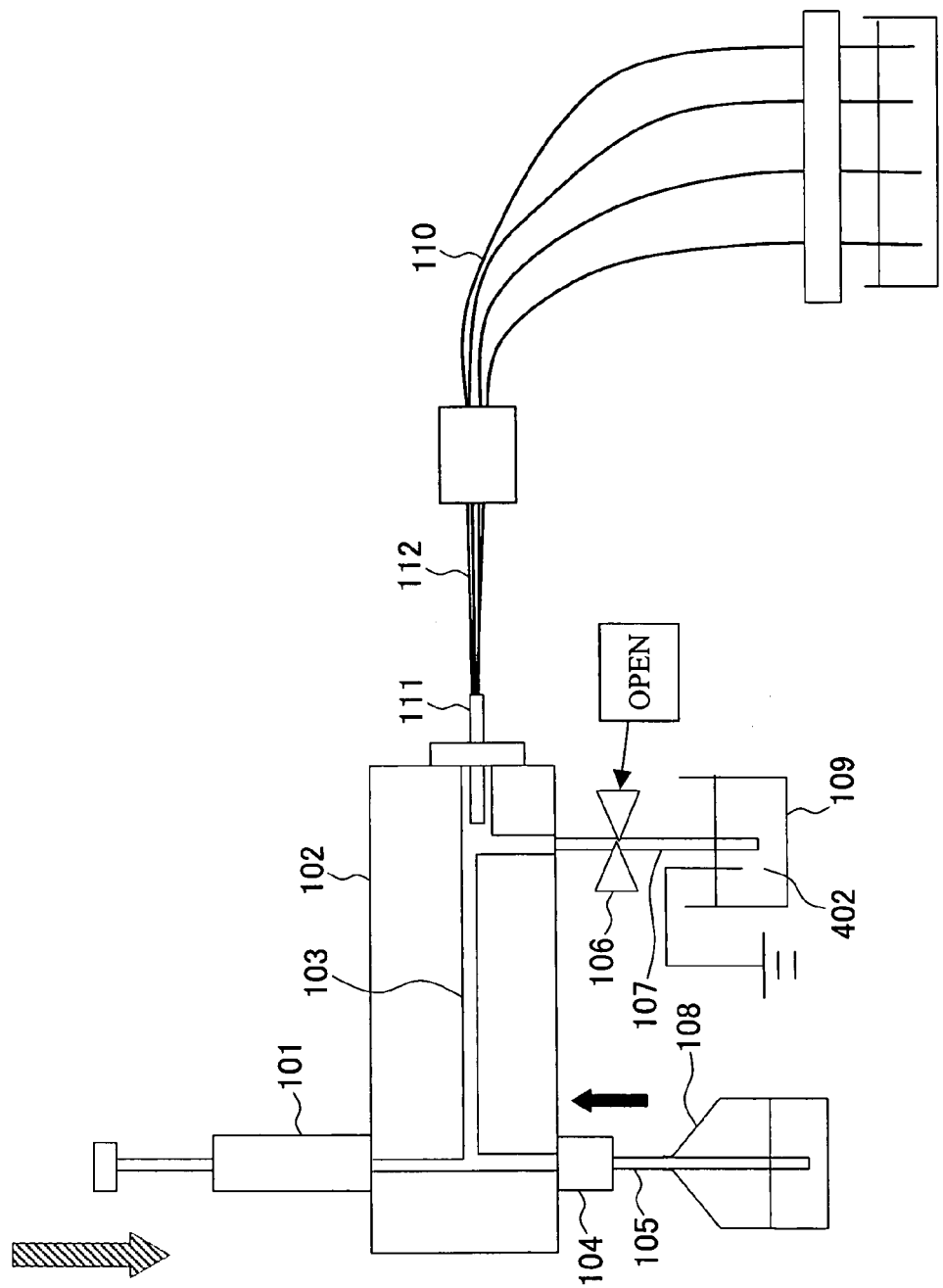
FIG. 4 is a diagram for explaining the method for filling the capillary with the polymer in the capillary electrophoresis apparatus according to the present invention.
Figure 5:
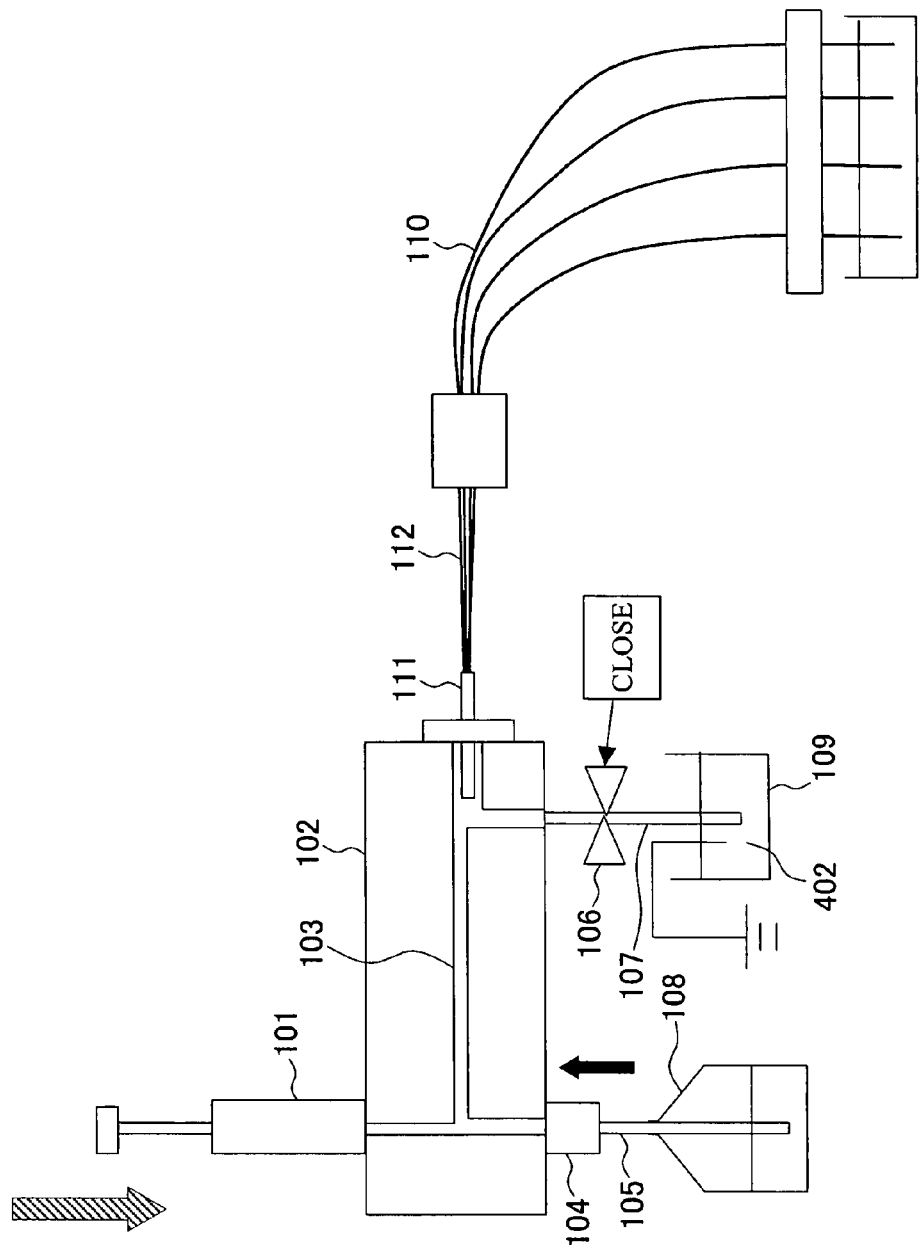
FIG. 5 is a diagram for explaining the method for filling the capillary with the polymer in the capillary electrophoresis apparatus according to the present invention.

With reference to FIGS. 3 to 5, the operation of the pump unit will be explained in detail. The pump unit includes the polymer block 102 with a minute pipe 103 formed in its inside. The upper end of the polymer block 102 is connected with the syringe 101. The lower end of the polymer block 102 is connected with pipes 105, 107. The pipe 105 having a check valve 104 has its lower end inserted to the polymer bottle 108. The pipe 107 having a channel switching valve 106 has its lower end inserted to the buffer container 109. The side end of the polymer block 102 is connected with a tube 111, and the tube 111 is connected with the capillary head 112. The syringe 101, the pipes 105, 107, and the tube 111 are connected with the minute pipe 103 of the polymer block 102.

Although the syringe 101 is used as a means for suctioning and ejecting the polymer for filling the capillary with the polymer in this example, other means for suctioning and ejecting a polymer such as a pump may be used as well. Moreover, the embodiment of the channel switching valve 106 such as a pin valve and a rotary valve is not limited. The anode 402 is soaked in the buffer in the buffer container 109.

FIG. 3 shows the state with the channel switching valve 106 closed and the plunger of the syringe 101 being pulled back to suction. The polymer in the polymer bottle 108 flows into the syringe 101 via the pipe 105, the check valve 104, and the minute pipe 103 in the polymer block 102. Thereby, the syringe 101 is filled with the polymer.

FIG. 4 shows the state with the channel switching valve 106 opened and the plunger of the syringe 101 being pushed down. The polymer in the syringe 101 flows into the buffer container 109 via the minute pipe 103 in the polymer block 102 and the channel switching valve 106. By flowing the polymer into the buffer container 109, the check valve 104 ejection side has the negative pressure so that the polymer in the polymer bottle 108 flows into the minute pipe 103 in the polymer block 102 via the check valve 104. Thereby, the minute pipe 103 in the polymer block 102 is filled with the polymer so as to eliminate the bubbles.

FIG. 5 shows the state with the channel switching valve 106 closed again and the plunger of the syringe 101 being pushed down. The polymer in the syringe 101 flows into the tube 111 via the minute pipe 103 in the polymer block 102, and furthermore, into the capillary. Since the channel switching valve 106 is closed, the polymer does not flow into the buffer container 109. By flowing the polymer into the capillary, the check valve 104 ejection side has the negative pressure so that the polymer in the polymer bottle 108 flows into the minute pipe 103 in the polymer block 102 via the check valve 104.

By flowing the polymer into the capillary, the used polymer in the capillary is discharged from the capillary end of sample injection.

In this example, the capillary is filled with the polymer by pressuring the minute pipe 103 in the polymer block 102 from the syringe 101 side. However, the method for filling the capillary with the polymer is not limited thereto. For example, the capillary may be filled with the polymer by soaking the sample injection end 204 of the capillary in a container filled with a new polymer and reducing the pressure of the minute pipe 103 in the polymer block 102 from the syringe 101 side.

Hereafter, with reference to FIGS. 6 to 8, examples of the polymer container in the present invention will be explained. The polymer container according to the present invention is used instead of the polymer bottle 108.

Figure 6:
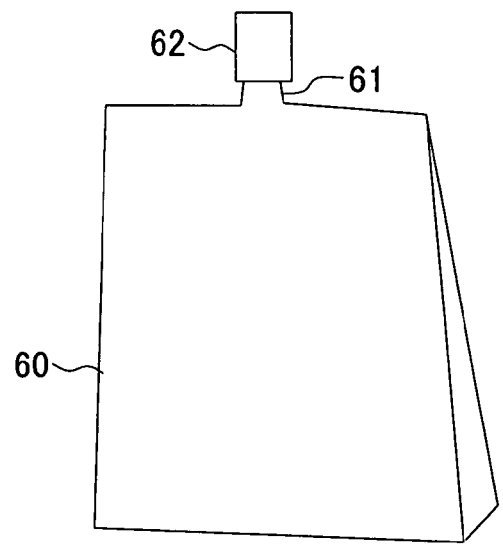
FIG. 6 is a diagram showing a first example of a polymer container of a capillary electrophoresis apparatus according to the present invention.
Figure 6:
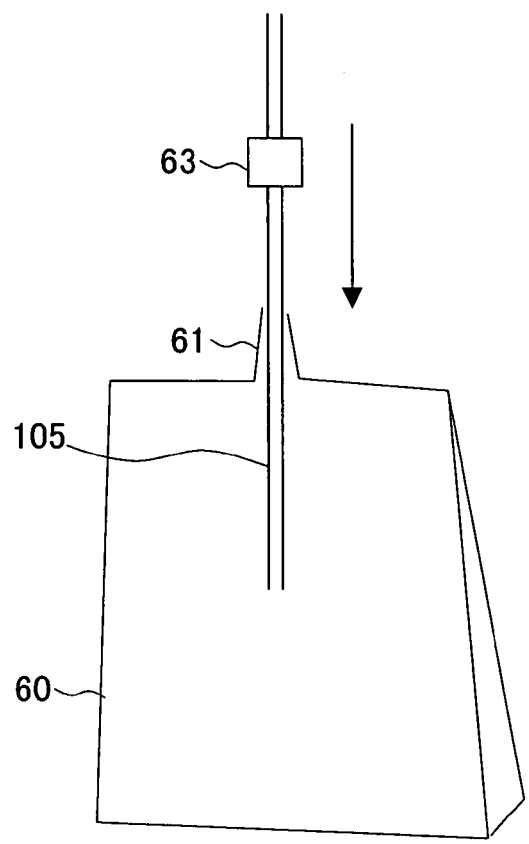

With reference to FIG. 6, a first example of the polymer container according to the present invention will be explained. The polymer container 60 of this example is formed as a flexible and preferably soft plastic bag or pouch. Instead of the plastic, a material with the light shielding property improved by laminating for example an aluminum onto the plastic may be used. Moreover, other flexible materials may be used. An opening 61 is formed in the upper part of the polymer container 60 with a cap 62 mounted on the opening 61. The thread is formed on the outer surface of the opening 61 so as to be engaged with the thread of the cap 62.

As shown in FIG. 6A, in the prior-to-use state, the polymer container 60 is filled with the polymer as a separation medium. The polymer container 60 is filled only with the polymer without the air sealed. That is, the polymer is vacuum-sealed in the polymer container 60. As shown in FIG. 6B, at the time of use, the cap 62 is removed so that the tube 105 for suctioning the polymer is inserted into the opening 61. Then, a fastening cap 63 mounted on the tube 105 is engaged with the opening 61. A thread to be engaged with the thread of the opening 61 is formed on the inner surface of the fastening cap 63. Thereby, the inside of the polymer container 60 is sealed by engaging the fastening cap 63 with the opening 61 in the upper part of the polymer container 60.

As shown in FIG. 3, when the pump is in the suction mode, the inside of the polymer container 60 is suctioned by the tube 105. Thereby, the polymer in the polymer container 60 flows into the tube 105. If the polymer in the polymer container 60 is reduced, the pressure in the polymer container 60 is reduced so that the polymer container 60 is crushed by the atmospheric pressure. However, the air does not flow into the polymer container 60. Accordingly, the polymer container 60 is shrunk and deformed until the all polymer in the polymer container 60 is suctioned.

Since the air does not flow into the polymer container 60 in this example, deterioration of the polymer in the polymer container 60 by oxidation cannot be caused. Therefore, the polymer in the polymer container 60 can be used up to the last drop. Thereby, according to the present invention, the polymer can be used efficiently without waste.

Figure 7:
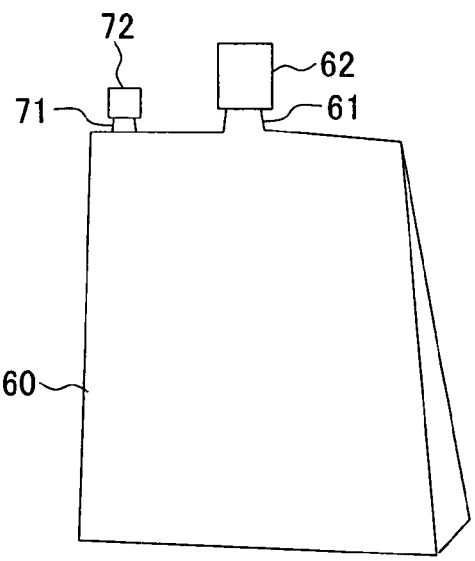
FIG. 7 is a diagram showing a second example of a polymer container of a capillary electrophoresis apparatus according to the present invention.
Figure 7:
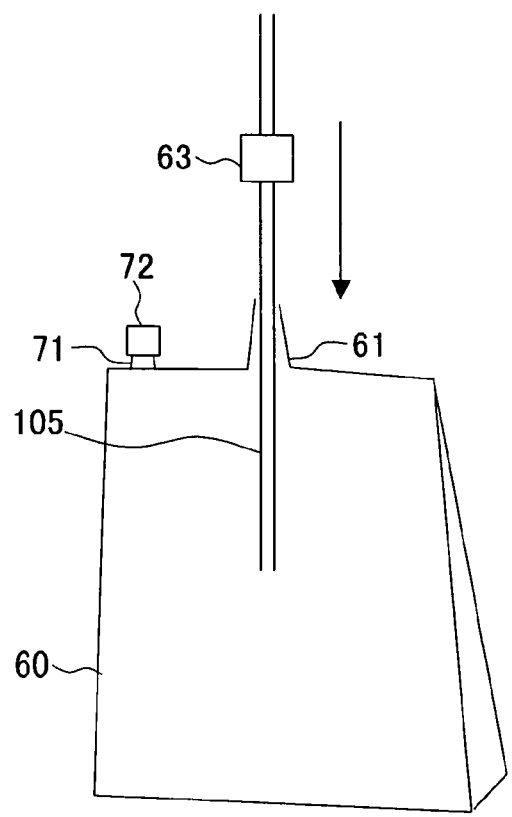

With reference to FIG. 7, another example of the polymer container according to the present invention will be explained. The polymer container 60 of this example has a vent 71 formed, with a cap 72 mounted on the vent 71. As mentioned above, the air is not introduced into the polymer container 60. However, the air may be introduced into the polymer container 60 inadvertently. According to the polymer container of this example, the air in the polymer container 60 can be discharged in such a case. After removing the cap 72, the polymer container 60 is pushed with hands from both sides for discharging the air in the inside. Instead of pushing the polymer container 60 with hands, or while pushing the polymer container 60 with hands, the air may be suctioned with a human mouth from the cap 72. The operation of discharging the air from the polymer container 60 may be carried out either before the use shown in FIG. 7A or during the use shown in FIG. 7A.

Figure 8:
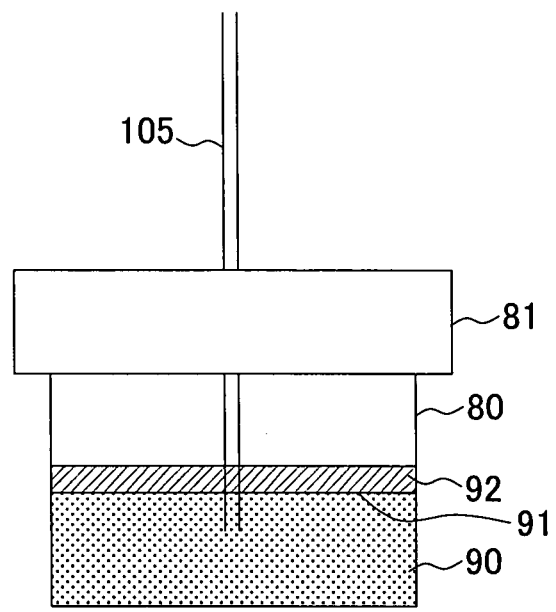
FIG. 8 is a diagram showing a third example of a polymer container of a capillary electrophoresis apparatus according to the present invention.

With reference to FIG. 8, still another example of the polymer container according to the present invention will be explained. The polymer container 80 of this example includes a wide opening bottle 80 and a lid 81 with a tube 105 for suctioning the polymer provided through the lid 81. The lid 81 made of an elastic material such as a rubber has the tube 105 provided through a hole formed therein. The inner diameter of the hole of the lid 81 is slightly smaller than the outer diameter of the tube 105. Therefore, the inside of the wide opening bottle 80 is sealed without a gap between the hole of the lid 81 and the tube 105.

The inside of the wide opening bottle 80 is filled with the polymer 90, with a drop lid 92 provided on the surface 91 of the polymer 90. The tube 105 is provided through the hole formed in the drop lid 92. Accordingly, since the surface 91 of the polymer 90 is covered with the drop lid 92 in this example, it is not contacted with the air. Therefore, the polymer 90 cannot be deteriorated by oxidization.

The drop lid 92 is formed of a material having a specific gravity smaller than that of the polymer so that it can float on the surface 91 of the polymer 90. The drop lid 92 is made from a substance unreactive with the polymer 90. The drop lid 92 may be formed of for example a foamed material.

The drop lid 92 may be mounted on the tube 105 for suctioning the polymer. However, the drop lid 92 may also be mounted on the wide opening bottle 80. In this case, the drop lid 92 may be mounted on the polymer container at the time of shipping from the polymer manufacturer, or it may be mounted on the polymer container by the user at the time of use. The drop lid 92 may either be of a disposable type or of a reusable type.

Although the drop lid 92 for covering the surface 91 of the polymer 90 is used here, instead of the drop lid 92, a liquid resin unreactive with the polymer 90 and having a specific gravity smaller than that of the polymer 90 may be used as well.

Although the examples of the present invention have been explained so far, the present invention is not limited to these examples, and it is easily understood by those skilled in the art that various modifications can be applied within the scope of the present invention disclosed in the claims.

What is claimed is:

1. A capillary electrophoresis apparatus comprising a capillary, a pump unit for filling the capillary with a separation medium, an irradiation and detection unit having a light source for irradiating an exciting light to a capillary detection area and a signal detecting mechanism for detecting a fluorescence from the capillary detection area, and a power supply unit for applying a voltage between a capillary end of sample injection side electrode and an anode, wherein the pump unit has a polymer container for storing a polymer as the separation medium, the polymer container being a sealed container having an opening and a cap to be engaged with the opening, the polymer container being formed of a flexible material, the pump unit having a syringe and a polymer block which has a pipe for connection between the syringe, the polymer container and the capillary, and wherein:

the polymer is sealed in the polymer container, the pump unit is configured to fill the capillary with the polymer separation medium via suction of the polymer from the polymer container, and to cause atmospheric pressure to crush the container by reducing pressure in the container so that air does not flow into the polymer container, the opening is sealed with a fastening cap with a tube provided therethrough when an open end of the tube is inserted through the opening of the polymer container, and the open end of the tube inserted through the opening of the polymer container is configured to reach only partially into the polymer container.

2. The capillary electrophoresis apparatus according to claim 1, wherein the polymer container is provided with a vent and a cap to be engaged with the vent.

3. The capillary electrophoresis apparatus according to claim 1, wherein the polymer container is formed as a pouch or a bag made of a plastic material.

* * * * *